United States Patent [19]
Sekine

[11] Patent Number: 5,066,116
[45] Date of Patent: Nov. 19, 1991

[54] OPTICAL SYSTEM IN A LASER SCANNING EYE FUNDUS CAMERA

[75] Inventor: Akihiko Sekine, Tokyo, Japan

[73] Assignee: Kabushiki Kaisha Topcon, Tokyo, Japan

[21] Appl. No.: 549,178

[22] Filed: Jul. 6, 1990

Related U.S. Application Data

[63] Continuation-in-part of Ser. No. 212,388, Jun. 27, 1988, Pat. No. 4,960,327.

[30] Foreign Application Priority Data

Jul. 15, 1987 [JP] Japan .................................. 62-176760
May 9, 1988 [JP] Japan .................................. 63-112070

[51] Int. Cl.$^5$ ............................................... A61B 3/10
[52] U.S. Cl. ..................................... 351/221; 351/205; 351/211
[58] Field of Search ............... 351/205, 206, 211, 221; 354/62; 606/4, 5, 6

[56] References Cited

U.S. PATENT DOCUMENTS 4,764,005 8/1988 Webb et al. ..................... 351/205

Primary Examiner—Rodney B. Bovernick
Attorney, Agent, or Firm—Finnegan, Henderson, Farabow, Garrett & Dunner

[57] ABSTRACT

The present invention relates to the optical system in a laser scanning eye fundus camera. The optical system comprises an illuminating optical system for scanning an eye fundus with an illuminating laser light beam from a light source using a light scanning device, a light receiving optical system for directing the reflected light from the eye fundus to a light receiving unit; a beam diameter adjusting system associated with the optical systems for adjusting the beam diameter of the laser beam or of the light for observation; and a system for interlocking the adjustment of the beam diameter adjusting system with the adjustment of the magnification adjusting system wherein an adjustments of the magnification adjusting system to increase the magnification causes the beam diameter adjusting system to be adjusted to reduce the beam diameter. Such arrangement according to the present invention allows the adjustment of the depth of field by adjusting the aperture diameter of the optical system by the beam diameter adjusting system so that a test or inspecption of uniform or even quality can be ensured for all subjects in spite of variations in their age, experience of medical or opthamological tests or inspections, or structure of the eye fundus.

26 Claims, 17 Drawing Sheets

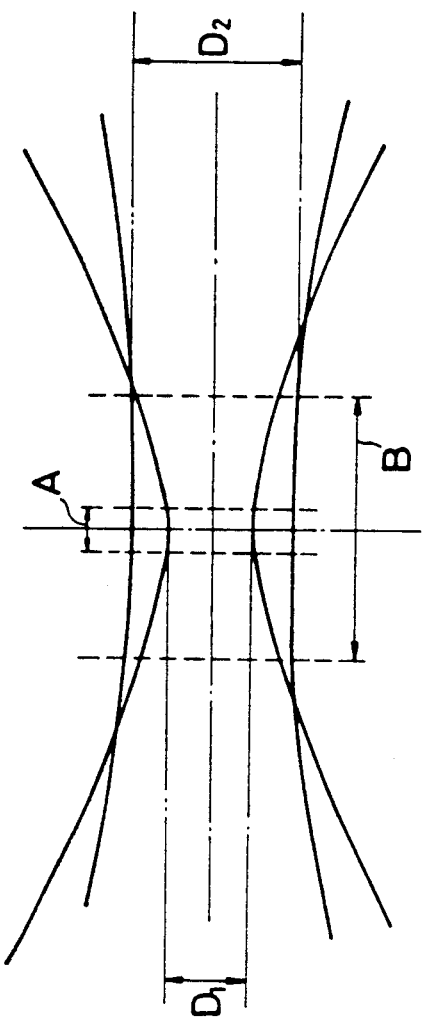
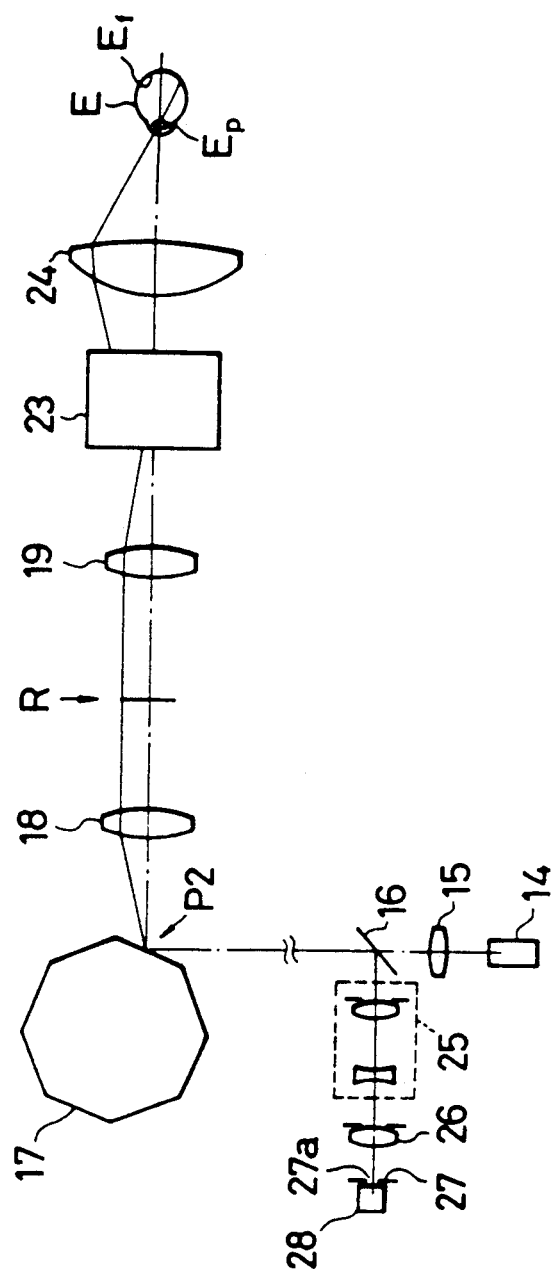

OPTICAL SYSTEM IN A LASER SCANNING EYE FUNDUS CAMERA

The present application is a continuation-in-part of U.S. patent application Ser. No. 212,388, filed on June 27, 1988 now U.S. Pat. No. 4,960,327.

BACKGROUND OF THE INVENTION

1. Field of the Invention

The present invention relates to the optical system in a laser scanning eye fundus camera which scans the fundus of a subject's eye with an illuminating laser beam.

2. Description of the Related Art

Conventional eye fundus cameras are arranged to uniformly illuminate the whole of the subject's eye fundus so as to observe or photograph it. The eye fundus must then be illuminated with a relatively intense flux of light which might regrettably cause pain to the subject.

In recent years, a new type of eye fundus camera has been developed which reduces such pain. It is adapted to scan the subject's eye fundus with an illuminating laser beam having a constant spot diameter and to detect the reflected light from the eye fundus at constant intervals, each interval being equal to the spot diameter of the laser beam. The data derived from the reflection due to spot illumination is used to construct an image of the fundus of the subject's eye on a monitor cathode ray tube (CRT).

Meanwhile, as illustrated in FIG. 4, the depth of focus for such a laser beam becomes shallower (space A) as the spot diameter, or the diameter of the cross section, of the laser light beam and hence the F-number are reduced (indicated by $D_1$). It conversely becomes deeper (space B) as the spot diameter and hence the F-number are increased (indicated by $D_2$).

The eye fundus is not smooth but rugged. To obtain a clear image of the eye fundus, therefore, the depth of focus for the laser beam should be deeper and hence the spot diameter of the laser beam should be larger to some extent.

In prior art apparatuses of the last-mentioned type, however, the laser beam diameter is invariably set to a very small value in order to obtain signals due to spot illumination greater in number than the number of picture elements of the associated monitor CRT. As a result, there is a problem with the prior art apparatus in that the depth of focus is relatively shallow and the image of the subject's eye fundus can become out of focus if the eye slightly moves relative to the apparatus. There is a tendency for young persons, in particular, to move the head or eyes while undergoing the ophthalmological inspection or test. Thus, it is desirable for the apparatus to have means for varying the spot diameter such that a clear image of the eye fundus can be obtained in spite of possible slight movement of the subject's eye relative to the apparatus. It is also desirable for the apparatus to be able to reduce the spot diameter so as to achieve a high resolution.

An eye fundus camera of such type is known in which, for purpose of achieving a high contrast image, a light beam scanning device is used by both an illuminating optical system for emitting a laser light beam, and a light receiving optical system for directing the reflected light or fluorescence from the eye fundus. In this eye fundus camera, a pin hole or diaphragm is provided in the light receiving optical system at a position which is optically conjugate with the eye fundus under test. The diameter of the pin hole determines the diameter of the spot of light projected onto the eye fundus, or the size of each picture element, whereby the resolution is determined.

In other words, the light receiving optical system of the eye fundus camera of the above-described type is designed such that only the light reflected from a particular region of the eye fundus, i.e., the region onto which an image of the pin hole is projected by the light receiving optical system, can pass through the pin hole. Thus, even if the illuminating light spot on the eye fundus is greater than the pin hole image on the eye fundus, the light reflected from outside the region of the pin hole image cannot pass through the pin hole. The resolution of the image of the eye fundus is therefore determined by the pin hole image on the eye fundus. Thus, the resolution of the apparatus of such an arrangement is determined by the optical system having the pin hole, i.e., the light receiving optical system.

In order that the eye fundus camera of such type can receive as large an amount of reflected light as possible at its light receiving part, and thereby have a high resolution, the diameter of the laser beam from the illuminating optical system should be variable in accordance with the scanning magnification for the subject's eye fundus, and further the diameter of the aperture of the light receiving optical system should be as large as possible.

There is however a problem in that, as the aperture diameter of the light receiving optical system is increased, the resolution becomes higher but at the same time the depth of field becomes shallower, with the result that the whole of the eye fundus cannot be in focus at one time and it will be out of focus due to only slight movement of the subject's eye relative to the apparatus.

SUMMARY OF THE INVENTION

The primary object of the present invention is therefore to provide an optical system in a laser scanning eye fundus camera which is capable of adjusting the depth of field so as to obtain an even or uniform quality of the ophthalmological inspection or test for all subjects in spite of variations between them in age, experience of ophthalmological inspection or test, or structure of the eye fundus, for example. In other words, the primary object of the present invention is to provide an optical system in a laser scanning eye fundus camera which is provided with adjusting means for adjusting at least one of the apertures of the illuminating and light-receiving systems thereby to adjust the depth of field, whereby an even or uniform quality of the ophthalmological inspection or test can be ensured for all subjects in spite of variations in their ages or conditions.

To achieve this object, the optical system in a laser scanning eye fundus camera according to the present invention is provided with an illuminating optical system for scanning an eye fundus with an illuminating laser beam from a light source using a light scanning device, a light receiving optical system for directing the reflected light from the eye fundus to a light receiving unit, and a beam diameter adjusting means associated with said optical system for adjusting the beam diameter of the laser beam or of the light for observation.

Another object of the present invention is to provide an optical system in a laser scanning eye fundus camera, in which the operator can change the spot diameter for a very young subject who is likely to move his eyes during the test or inspection, whereby a clear image of the eye fundus can be obtained in spite of slight movement of the subject's eye. A further object of the present invention is to provide an optical system in a laser scanning eye fundus camera which is capable of reducing the spot diameter so as to obtain a high resolution.

To achieve this object, and in view of the fact that the spot diameter, which is affected by the beam diameter, affects the depth of field, the present invention provides the illuminating optical system with spot diameter adjusting means for allowing the operator to adjust the spot diameter as necessary.

A still further object to the present invention is to provide an optical system in a laser scanning eye fundus camera which allows one to obtain a high resolution by means of the light receiving optical system.

To achieve this object, the present invention provides the light receiving optical system with beam diameter adjusting means.

Yet another object of the invention is to provide an optical system in a laser scanning eye fundus camera comprising an illuminating optical system for illuminating an eye fundus through an eye pupil by scanning the eye fundus with an illuminating laser light from a laser light source by means of an optical scanning device, a light receiving optical system for conducting the light reflected from the eye fundus to a light receiving optical system, the light receiving optical system includes a display device for displaying an image of the eye fundus in response to a signal from the light receiving system, the display device including magnification adjusting means for changing the magnification of the image of the eye fundus on said display device, beam diameter adjusting means provided in said illuminating optical system conjugate with the pupil for adjusting the beam diameter of the laser beam projected onto the eye fundus, and means for interlocking the adjustment of said beam diameter adjusting means with the adjustment of said magnification adjusting means wherein an adjustment of said magnification adjusting means to increase the magnification causes said beam diameter adjusting means to be adjusted to reduce the beam diameter.

Other objects and features of the invention will readily be understood from the following detailed description and the accompanying drawings.

BRIEF DESCRIPTION OF THE DRAWINGS

FIG. 4 is an illustration showing the relationship between the diameter of the laser beam and the depth of focus;

FIG. 5 is a schematic plan view showing the arrangement of another embodiment of the optical system in the laser scanning eye fundus camera according to the present invention;

DESCRIPTION OF THE PREFERRED EMBODIMENTS

A preferred embodiment of the present invention will now be described with reference of FIGS. 1 through 4.

Figure 1:
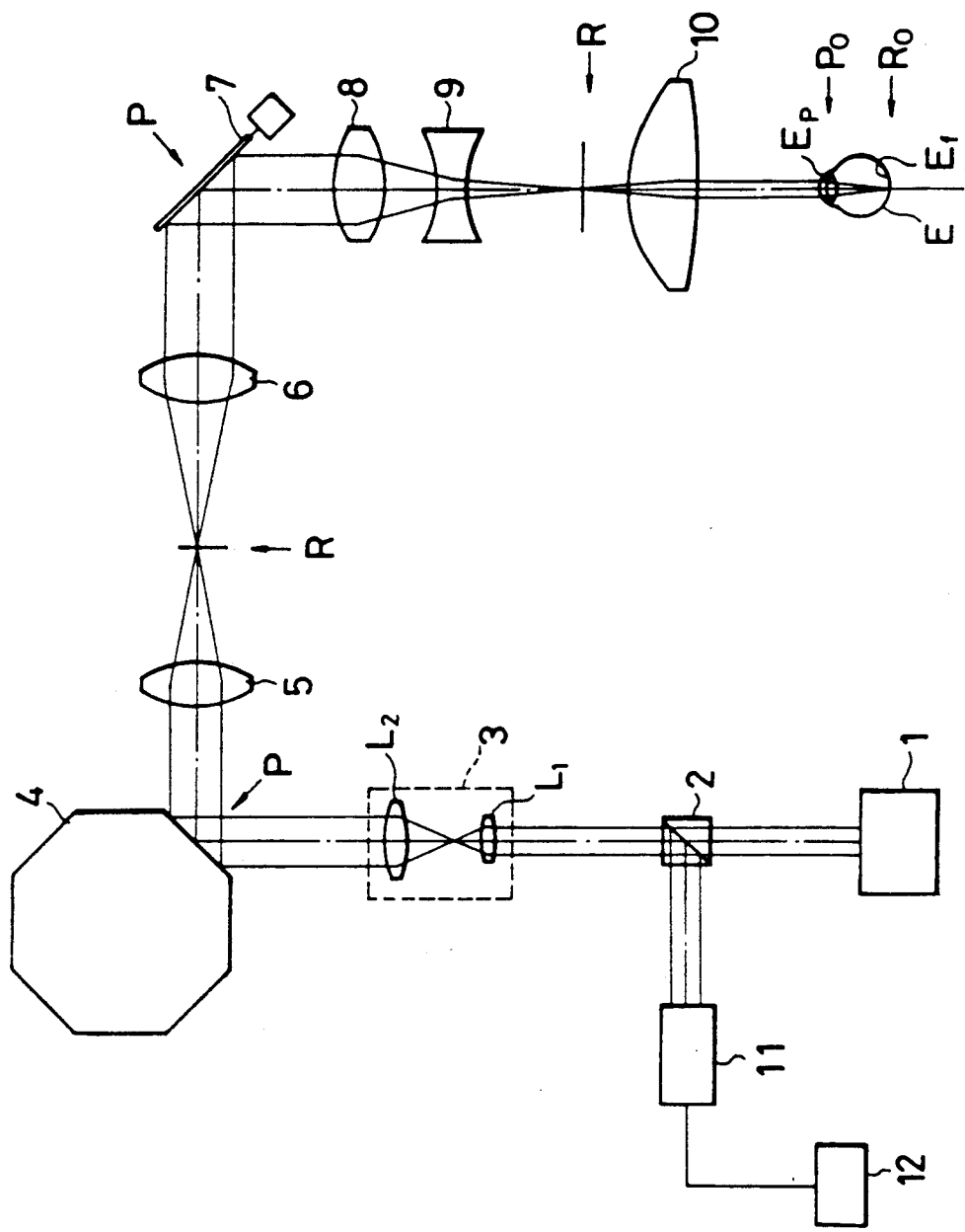
FIG. 1 is an illustration of an embodiment of the optical system in the laser scanning eye fundus camera according to the present invention.

FIG. 1 shows an embodiment of the optical system in a laser scanning eye fundus camera according to the present invention. The optical system of the eye fundus camera shown in FIG. 1 has an illuminating optical system for scanning the eye fundus $E_f$ of a subject's eye E with an illuminating laser beam, and a light receiving optical system for directing the reflected light from the eye fundus $E_f$ to a light receiving unit.

The illuminating optical system comprises a laser 1, a beam splitter 2, beam diameter adjusting means or spot diameter adjusting means in the form of a beam expander 3, a horizontal scanning member in the form of a polygonal mirror 4, variable power lenses 5 and 6, a vertical scanning member in the form of a galvanomirror 7, a relay lens 8, a focusing lens 9, and an objective lens 10. These elements are arranged in the order in which they are mentioned. In FIG. 1, P indicates a position which is conjugate with the pupil $E_p(P_o)$ of the subject's eye E, and R indicates another position which is conjugate with the eye fundus $E_f(R_o)$ of the subject's eye E.

In the illuminating optical system, the laser light beam generated by the laser 1 passes through the beam splitter 2 and then the diameter of the beam is varied by the beam expander 3. As shown, the beam expander 3 is removably placed in the optical path between the beam splitter 2 and the polygonal mirror 4. Further, the beam expander 3 is provided in a position which is conjugate with the pupil $E_p$ of the subject's eye E. The laser light beam having a diameter varied by the beam expander 3 impinges upon the polygonal mirror 4. The polygonal mirror 4 is driven by a motor (not shown) for rotation at a high speed, and reflects the laser beam from the beam expander 3 for scanning in a horizontal plane. The reflected laser beam passes through the variable power lenses 5, 6 and then impinges on the galvanomirror 7. The mirror 7 is rotated through a predetermined angle in one direction to thereby deflect the laser beam in a vertical direction each time a horizontal scanning by the polygonal mirror 4 has been completed. The galvanomirror 7 is rotated back to the original position after a predetermined number of rotations have been completed, thereby scanning for one frame. Scanning for the next frame is then initiated.

The laser light reflected from the mirror 7 is projected onto the fundus $E_f$ of the subject's eye E through the relay lens 8, focus lens 9, and objective lens 10. Thus, the eye fundus $E_f$ of the subject's eye E is sequentially scanned with the laser light beam generated by the laser 1, which light beam produces a spot of constant diameter on the eye fundus. The operator can vary the spot diameter at will by replacing the beam expander 3 in the illuminating optical path with another beam expander.

The light receiving optical system shares most of its optical path with the illuminating optical system, and it uses the optical path extending between the objective lens and the beam splitter 2. The reflected light from the eye fundus $E_f$ of the subject's eye E passes through the light receiving optical system and reaches the light receiving unit in the form of a photomultiplier tube 11. The output signal from the photomultiplier tube 11 is picked up at intervals of the spot diameter by a microcomputer (not shown), and each of the thus picked up signals is stored in the memory (not shown) as a picture element. Thus, data corresponding to picture elements are sequentially stored in the memory and once the stored data is sufficient to construct one frame, the data of one-frame picture elements are sequentially transferred to a monitor CRT 12. An image of the eye fundus is thus constructed on the monitor CRT 12.

Figure 2:
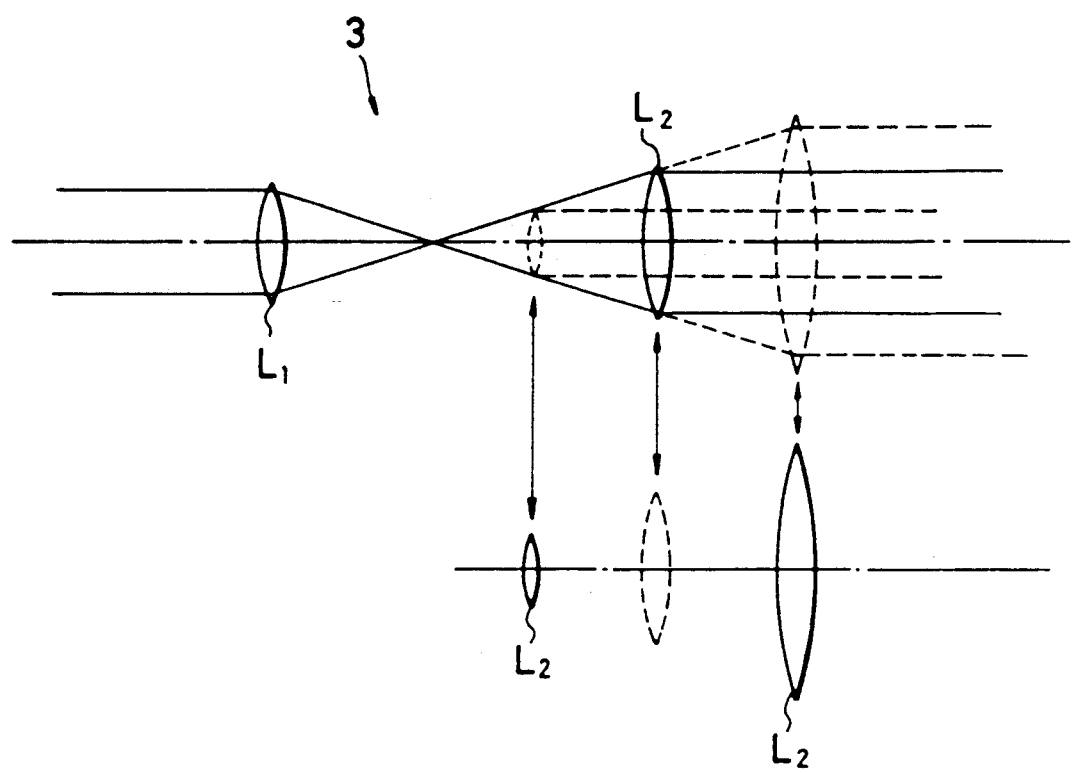
FIG. 2 is an illustration showing an alternative example of the beam expander shown in FIG. 1.
Figure 3:
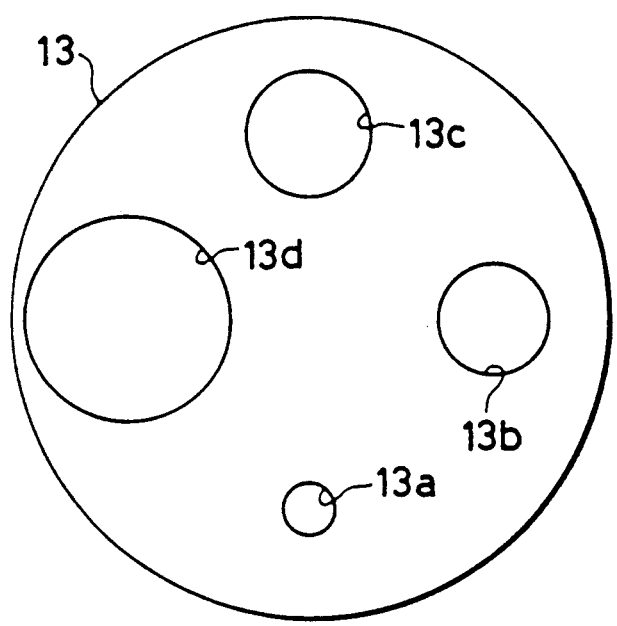
FIG. 3 is a plan view of an aperture plate which can be used in place of the beam expander shown in FIG. 1.

In the above-described embodiment, the beam expander 3 is interchangeable in its entirety with a substitute beam expander, but the present invention is not limited to such an arrangement. For example, an alternative embodiment of the beam expander 3 is shown in FIG. 2 and comprises two lens elements $L_1$ and $L_2$, of which the latter element $L_2$ can be selected from a set of alternative lenses which have different focal lengths and which can be removably placed in the optical path. In this example, the beam diameter can be changed in accordance with the alternative lens selected. Another alternative embodiment of the beam expander 3 is shown in FIG. 3, which comprises an aperture plate 13 having a plurality of apertures 13a, 13b, 13c, 13d of different diameters which can be selectively positioned in the optical path. Further, the beam expander 3 may be replaced by a zoom, i.e. variable power, optical system which provides an infinite number of different beam diameters within the power range of the system.

Meanwhile, when observation is performed at a high magnification using a variable power device capable of high magnification, the image may sometimes be partially indistinct since eye fundi are not smooth but rugged.

For such purpose, therefore, the spot diameter adjusting means should be arranged such that it allows the operator to vary the beam diameter at will and, when the magnification for observation is changed, the spot diameter is automatically varied by an amount which corresponds in some manner to the change in magnification.

Using the so arranged spot diameter adjusting means, the spot diameter is enlarged and the depth of focus is increased when the magnification is increased, so that all portions of the image within the observed region can be sharply focused.

The depth of focus when light of beam diameter D is made incident on the eye or exits from the pupil of the eye after being reflected from the eye fundus may be derived as follows:

If the distance from the equivalent principal plane of the eye is represented by L, the numeric value corresponding to the lens F number is L/D.

The depth of focus of the lens, if the observation wavelength is represented by $\lambda$, can be generally expressed as follows:

$$\text{depth of focus} = \pm 2\ F^2\lambda$$

(where F denotes the F number).

Therefore, the depth of focus at the eye fundus in the eye can be expressed as follows:

$$\text{depth of focus} = \pm 2\ (L/D)^2\lambda$$

Therefore, when a narrow angle of view (high power) is compared with the wide angle of view (low power), the depth of focus becomes shallower as the diameter D of the light beam becomes larger. The relation between the F number, diameter of the spot formed, and the light beam diameter D may be described as follows: If the light beam diameter D is large, the F number and the spot diameter becomes small. Conversely, if the light beam diameter is small, the F number and the spot diameter become large.

Often, the eye fundus has large irregularities and the tissue is of a layered structure. Therefore, the fluctuation of the depth of focus caused by the variable power may cause the portion of the eye fundus being observed to be out of focus. In addition, when the eye fundus is tested, it is easier to initially test the eye fundus with the wide angle of view (lower power) and then increase the power in order to test in detail. In that case, the increase of power reduces the depth of focus.

Therefore, it is desirable that the increase and decrease of the depth of focus accompanied by the variation in power be eliminated so that an eye fundus image with the same depth of focus can be obtained at any power. Furthermore, it is desirable that the depth of focus accompanied by this power change is automatically corrected so that it remains constant. Various structural embodiments for correcting the depth of focus will be described with reference to FIGS. 16–27. In order to selectively insert the lens $L_2$ of FIG. 2 into the optical path, or remove the lens $L_2$ of FIG. 2 to and from the optical path, a structure as shown in FIGS. 16 through 20 may be employed.

Figure 17:
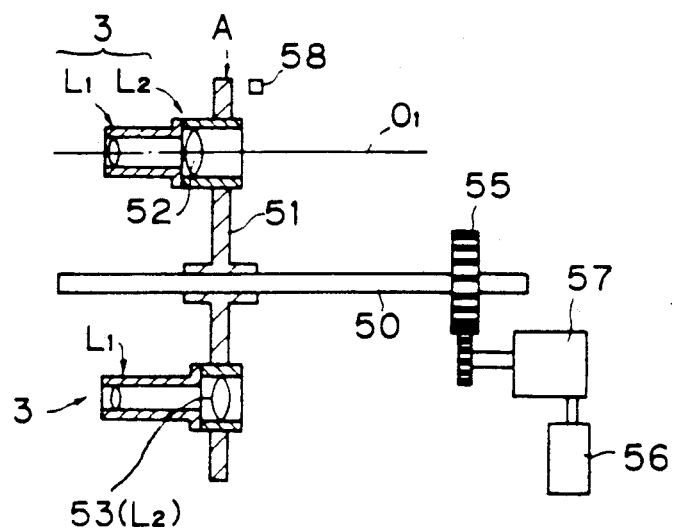
FIG. 17 is a side view of a light beam diameter changing element in accordance with the present invention.
Figure 18:
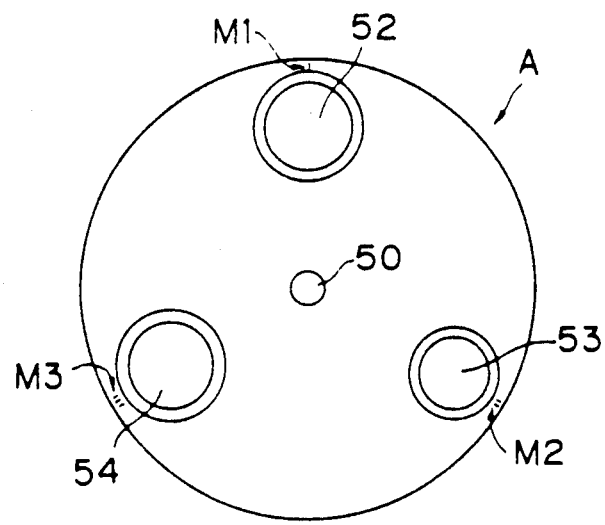
FIG. 18 is a top view of the rotatable disk shown in FIG. 17.

In this example as illustrated in FIG. 17, a rotatable disk 51 is fixed to a rotational shaft 50 which is parallel to the optical axis $O_1$ of the beam expander 3. A number of beam expanders having different focal lengths are mounted on this rotatable disk 51 as shown in FIG. 18. Each of the beam expanders 3 comprises a combination of a lens $L_1$ with any of the lenses 52, 53 and 54, each having different focal lengths. The rotatable disk 51, the lens $L_1$, and the lenses 52, 53 and 54 form the light beam diameter changing element A. The lenses 52, 53 and 54 are used as the lens $L_2$ of FIG. 2.

Also, a gear 55 is fixed to the rotational shaft 50, and a motor 56 acting as a driving apparatus is connected to the gear 55 through the gear reducer 57. Moreover, an optical sensor 58 acting as a light beam diameter detecting portion is disposed to the side of the peripheral portion of the rotatable disk 51. Furthermore, the rotational disk 51 is provided with the lens identification marks such as the light beam diameter identification marks M1, M2 and M3 attached to the peripheral portion thereof at places corresponding to the respective lenses 52, 53 and 54. The optical sensor 58 generates output signals corresponding to the marks M1, M2 and M3.

Figure 19:
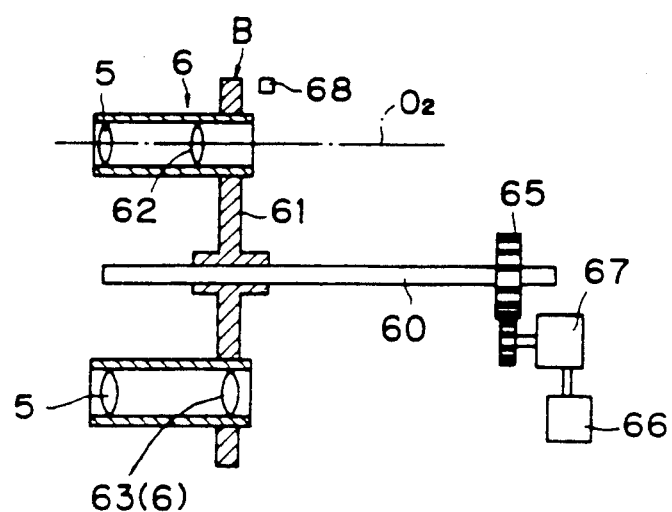
FIG. 19 is a side view of an observation power changing element in accordance with the present invention.
Figure 20:
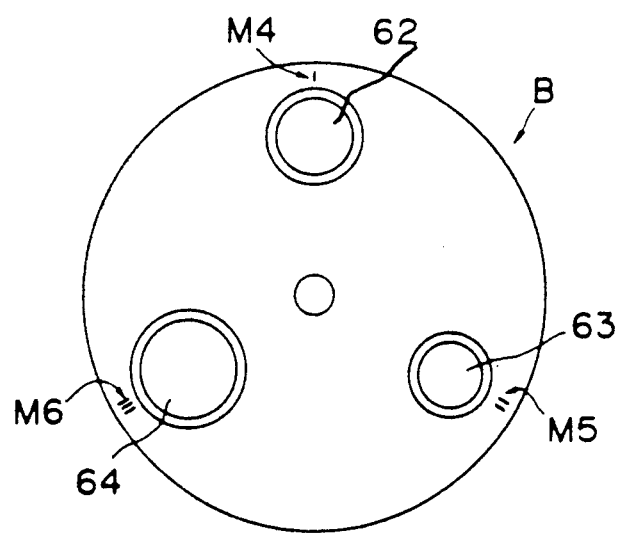
FIG. 20 is a top view of the rotatable disk shown in FIG. 19.

As shown in FIG. 19, rotatable disk 61 is fixed to the rotational shaft 60 parallel to the optical axis $O_2$ of the variable lenses 5 and 6. Lenses 62, 63 and 64, each having different focal lengths and acting as the variable lens 6 of FIG. 1 are mounted on this rotatable disk 61 as shown in FIG. 20. Each of the lenses 62, 63 and 64 is used as one set with the variable lens 5. The rotatable disk 61, the variable lens 5 and the lenses 62, 63 and 64 are used as the observation power changing element B, while the lenses 62, 63 and 64 are used as the variable lens 6 of FIG. 1. A gear 65 is fixed to the rotational shaft 60, and a motor 66 acting as a driving apparatus is connected to this gear 65 through the gear reducer 67. Moreover, an optical sensor 68 acting as a light beam diameter detecting portion is disposed near the peripheral portion of the rotatable disk 61. The rotatable disk 61 is provided with lens identification marks such that the observation power identification marks M4, M5 and M6 attached to peripheral portions correspond to the lenses 62, 63 and 64. The optical sensor 68 generates output signals corresponding to the marks M4, M5 and M6.

Detection signals from the optical sensors 58 and 68 are input into the light beam diameter selecting circuit 70. The light beam diameter selecting circuit 70 can identify which of the lenses 52, 53, or 54, and which of the lenses 62, 63 or 64 are inserted in the optical paths. Moreover, this light beam diameter selecting circuit 70 controls the motor 56 through the driver 71 as follows.

When any of the lenses 62, 63 or 64 is selectively inserted into the optical path by rotating the rotatable disk 61 by actuating the motor 66, the light beam diameter selecting circuit 70 identifies which of the variable lenses 62, 63 or 64 is located in the optical path in accordance with the detection signal from the optical sensor 68. The light beam diameter selecting circuit 70 thereby identifies the selected variable lens 62, 63, or 64 and the observing power by the variable lens 5. The light beam diameter selecting circuit 70 actuates the motor 56 through the driver 71 to thereby rotate the rotatable disk 51. At this time, the optical sensor 58 detects any of the marks M1, M2 and M3. The detected signal is input into the light beam diameter selecting circuit 70, and the light beam diameter selecting circuit 70 causes the motor 56 to stop when the input detection signal corresponds to the target beam diameter. Change of the beam diameter by such control is performed in such a manner as to reduce the beam diameter when the observing power becomes large (that is, when the observing range becomes narrow), and increase the beam diameter when the observing power becomes small (that is, when the observing range becomes wide). Such change can be effected with ease by previously selecting the combination of the lens 52, 53 and 54 with the lenses 62, 63 and 64.

Figure 21:
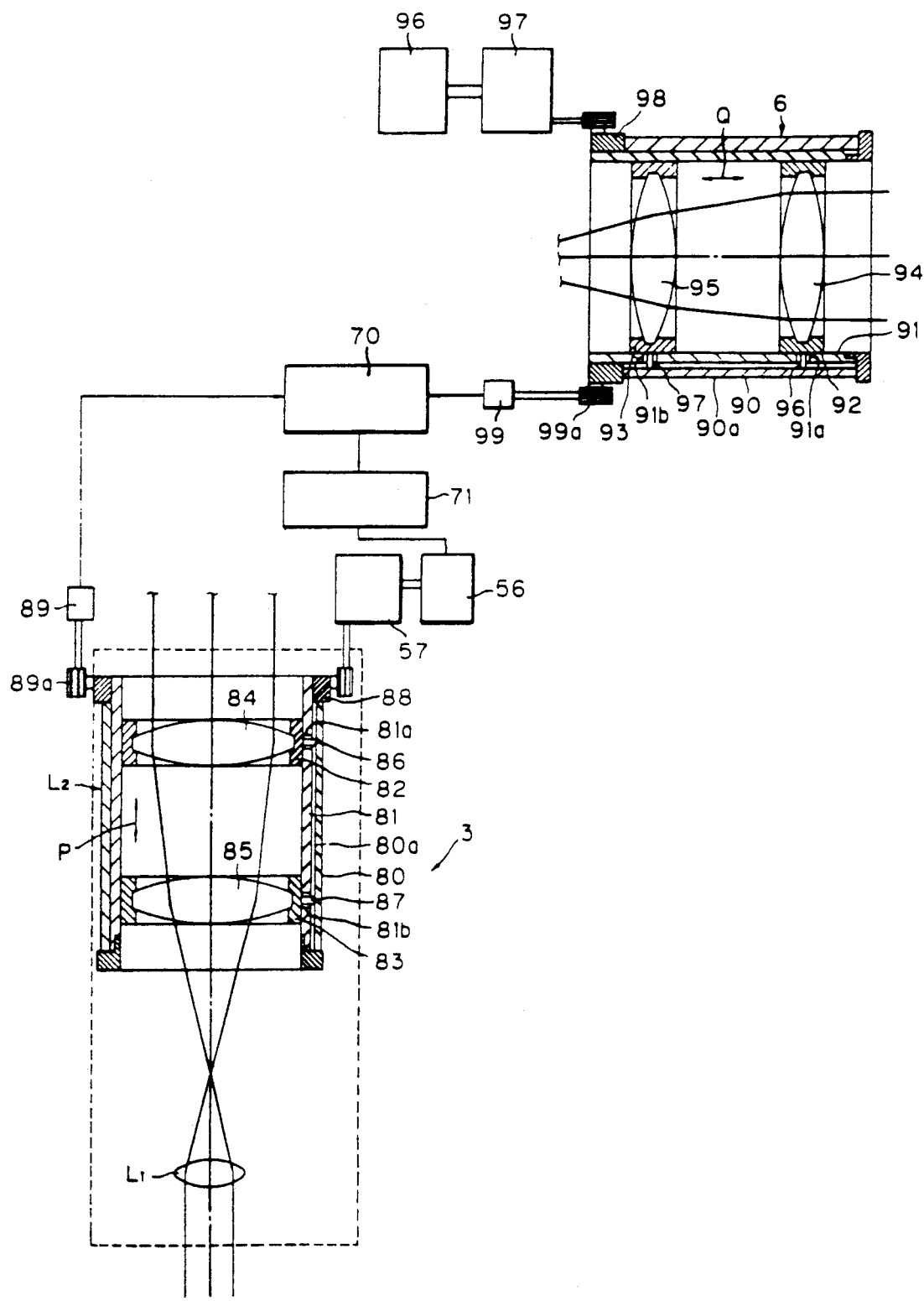
FIG. 21 is a side view of a further embodiment of the present invention.

FIG. 21 shows an embodiment in which the change of the observing power and the beam diameter can be effected steplessly and continuously.

In this example, the lens $L_2$ acting as the light beam diameter changing element has a fixed inner barrel 80, a cam drum 81 supported within the fixed inner barrel 80 in such a manner as to be rotatable but unmovable in the axial direction, lens frames 82 and 83 movably disposed within the cam drum 81 for movement in the axial direction, and lenses 84 and 85 held by the lens frames 82 and 83.

Moreover, the cam drum 81 has cam slits 81a and 81b formed thereon and spirally extending in the axial and circumferential directions. Pins 86 and 87 mounted on the lens frames 82 and 83 are engaged in the cam slits 81a and 81b. Also, the fixed inner barrel 80 has a key groove 80a formed in the inner surface thereof and extending in the axial direction. The tip portion of pins 86 and 87 are engaged in the key groove 80a. When the cam drum 81 is rotated by the function of the cam slits 81a and 81b, the pins 86 and 87, and the key groove 80a, the lens frames 82 and 83 and the lenses 84 and 85 are moved in the axial direction as shown by the arrow P, and the beam diameter is steplessly changed.

Furthermore, the cam drum 81 is provided with a gear 88. This gear 88 is connected with the motor 56 through the gear reducer 57 and further with the rotary encoder 89 through a gear 89a.

The motor 56 is actuated to transmit the rotation of the motor 56 to the cam drum 81 through the gear reducer 57.

The variable lens 6 has a fixed inner barrel 90, a cam drum 91 supported within the fixed barrel 90 in such a manner as to be rotatable but unmovable in the axial direction, lens frames 92 and 93 disposed within the cam drum 91 in such a manner as to be movable in the axial direction but non-rotatable in the circumferential direction, and lenses 94 and 95 held by the lens frames 92 and 93. Moreover, the cam drum 91 has cam slits 91a and 91b formed thereon and spirally extending in the axial and circumferential directions. Pins 96 and 97 mounted on the lens frames 92 and 93 are engaged in the cam slits 91a and 91b.

The fixed inner barrel 90 has a key groove 90a formed in the inner surface thereof and extending in the axial direction. The tip portions of pins 96 and 97 are engaged in the key groove 90a. When the cam drum 91 is rotated by the function of the cam slits 91a and 91b, the pins 96 and 97, and the key groove 90a, the lens frames 92 and 93 and the lenses 94 and 95 are moved in the axial direction as shown by the arrow Q, and the observing power is steplessly changed.

Furthermore, the cam drum 91 is provided with a gear 98. This gear 98 is connected with the motor 66 through the gear reducer 67 and further with a rotary encoder 99 acting as observation power detecting means through a gear 99a.

A detection signal from the rotary encoders 89 and 99 is input into the light beam diameter selecting circuit 70. The light beam diameter selecting circuit 70 is adapted to calculate the beam diameter with reference to the detection signal from the rotary encoder 89 and also calculate the observing power with reference to the detection signal from the rotary encoder 99. Moreover, when the light beam diameter selecting circuit 70 causes the motor 66 to rotate the cam drum 91 to change the observing power, it controls the motor 56 through the driver 71 and controls the rotation of the cam drum 81.

The change of the beam diameter caused by such control is set such that when the observing power is increased by the variable lenses 5 and 6 (i.e., when the observing range is reduced), the beam diameter is reduced, and when the observing power is reduced by the variable lenses 5 and 6 (i.e., when the observing range is increased), the beam diameter is increased.

Figure 22:
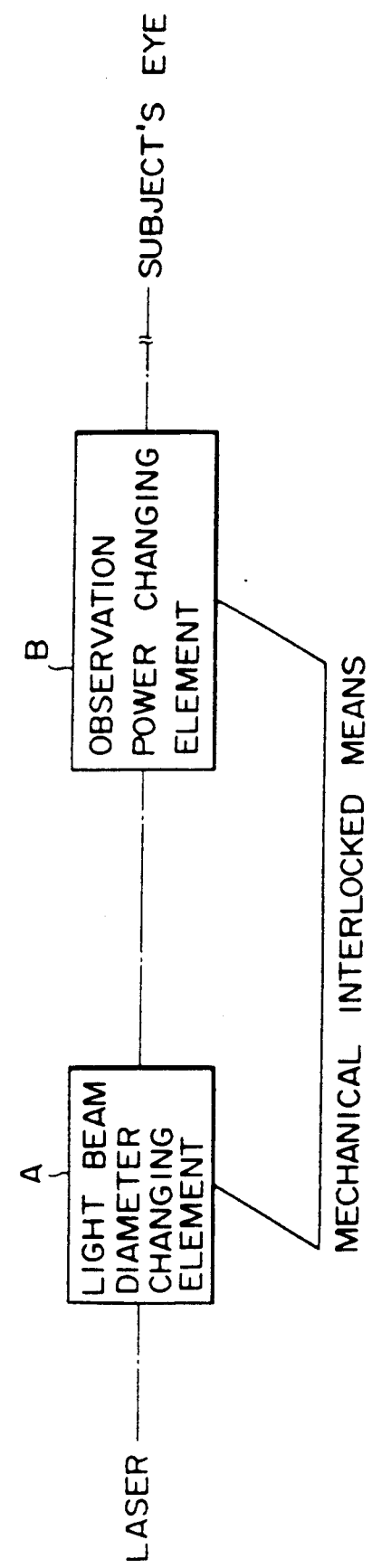
FIG. 22 is a block diagram of a further embodiment of the present invention.
Figure 23:
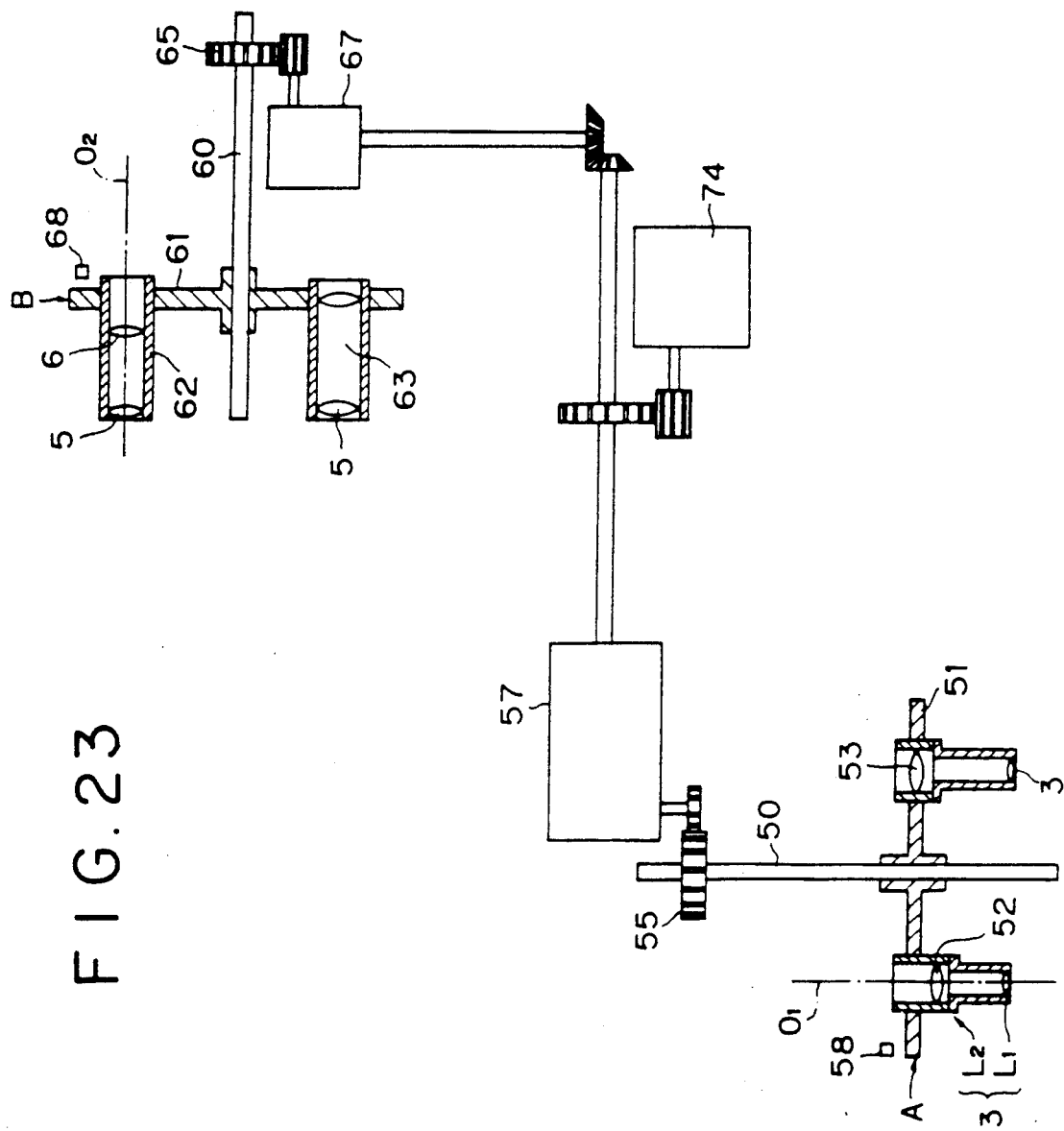
FIG. 23 is a side view of still a further embodiment of the present invention.

FIGS. 22 and 23 show one example in which the gear reducers 57 and 67 of FIGS. 17 and 19 are controlled by a single motor 74. In this example, by initially selecting the corresponding relation between the combination of the lenses 52, 53 and 54 and the lenses 62, 63 and 64 and the gear reducers 57 and 67, the change of the beam diameter with respect to the change of the observing power can be effected with ease. The similar elements shown in FIGS. 22-27 have been previously described and therefore will not be discussed further.

Figure 24:
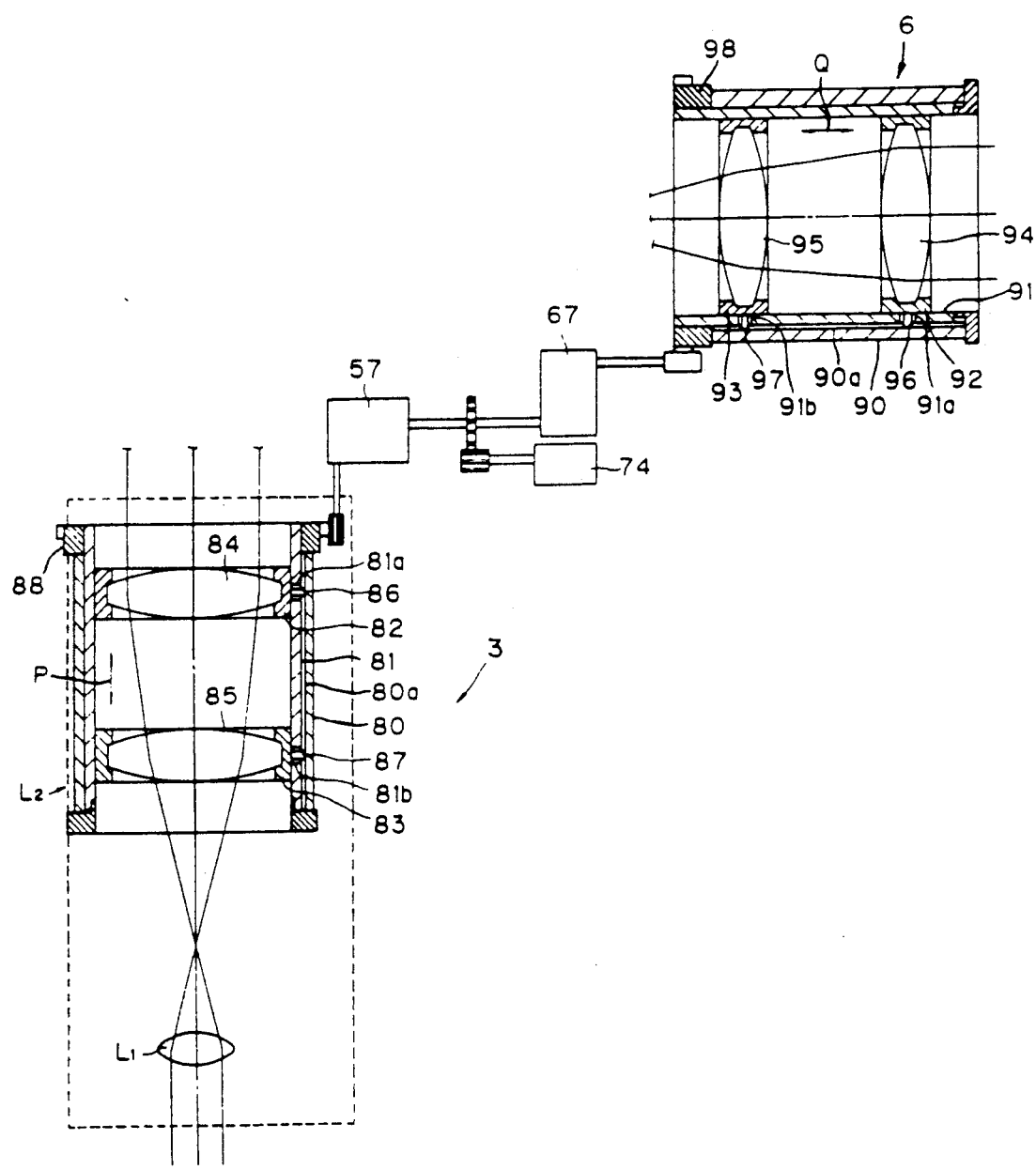
FIG. 24 is a side view of another embodiment of the present invention.

FIG. 24 shows another example in which the gear reducers 57 and 67 of FIG. 21 are controlled by a single motor 74. In this example, by initially selecting a certain corresponding relation between the change of the observing power caused by the variable lens 6 and the change of the beam diameter caused by the lens 12 acting as a light beam diameter changing element, a desirable change of the beam diameter and the observing power can be effected with ease.

Figure 25:
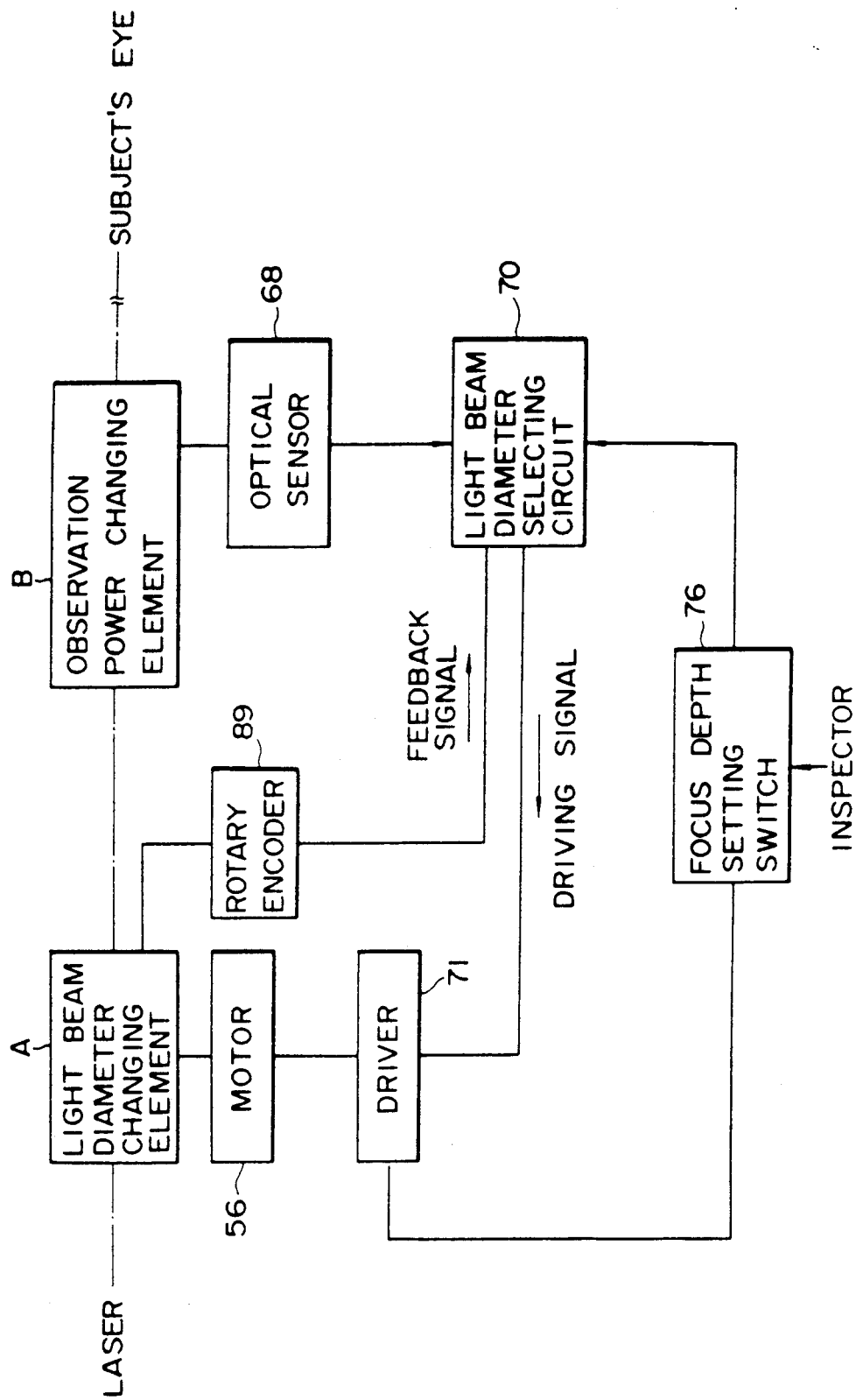
FIG. 25 is a block diagram of another embodiment of the present invention.
Figure 26:
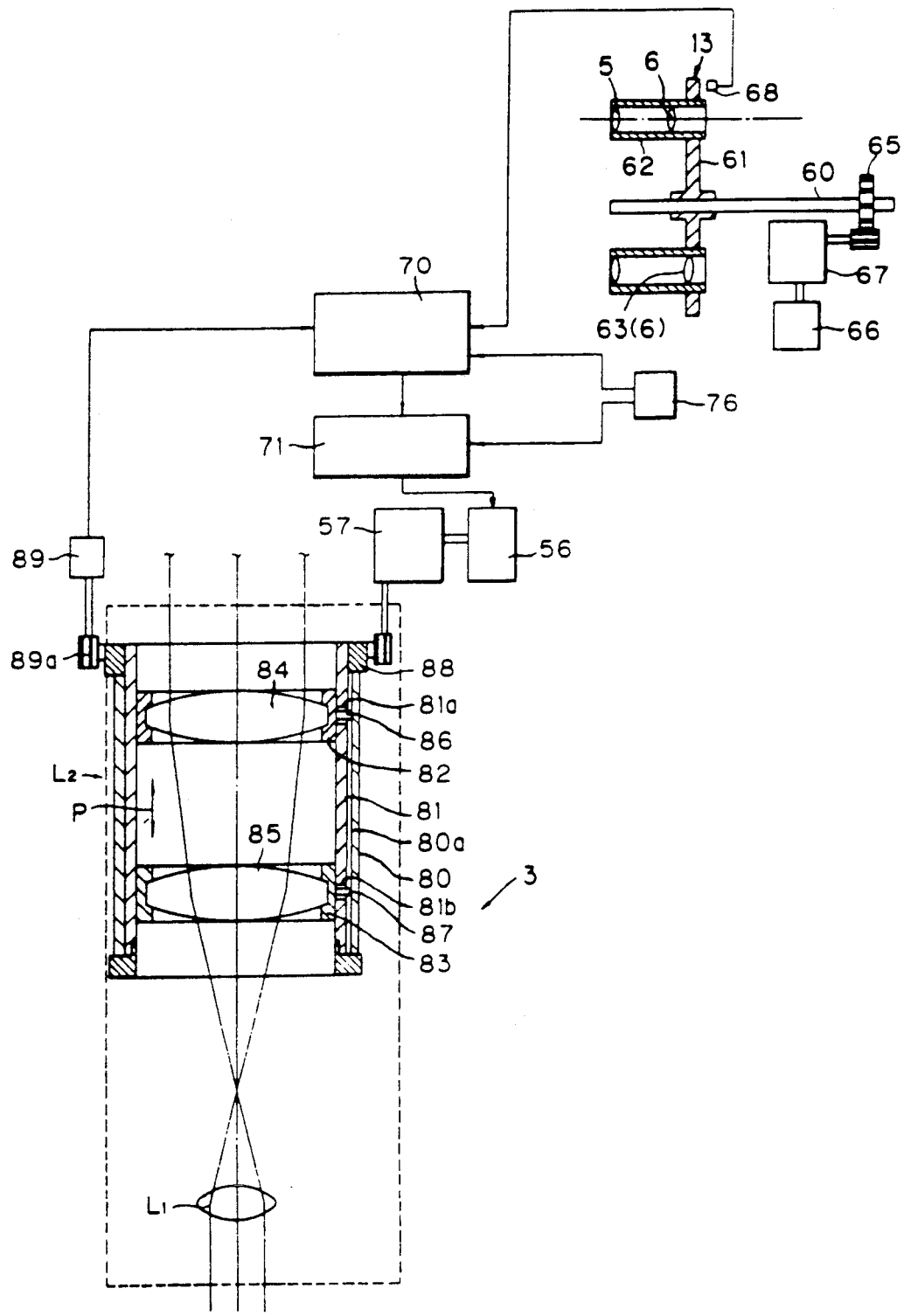
FIG. 26 is a side view of still another embodiment of the present invention.

FIGS. 25 and 26 show still another embodiment, in which the optical changing element in the embodiment of FIGS. 16 through 20 is replaced with the lens $L_2$ of FIG. 21 and a focus depth setting switch 76 for adjusting the depth of focus by optionally setting the beam diameter with respect to the observing power is employed. In this example, the inspector can desirably set the beam diameter with respect to the observing power when the lenses 62, 63 and 64 are inserted into the optical path. The light beam diameter circuit 70 is adapted to determine which of the lenses 62, 63 or 64 is inserted in the optical path with reference to the detecting signal from the optical sensor 68 and calculate the previously set beam diameter. Based on such calculation result, the beam diameter selecting circuit 70 causes the driver 71 to control the motor 56 in order to control the rotation of the lens $L_2$, thereby to determine the beam diameter.

Figure 27:
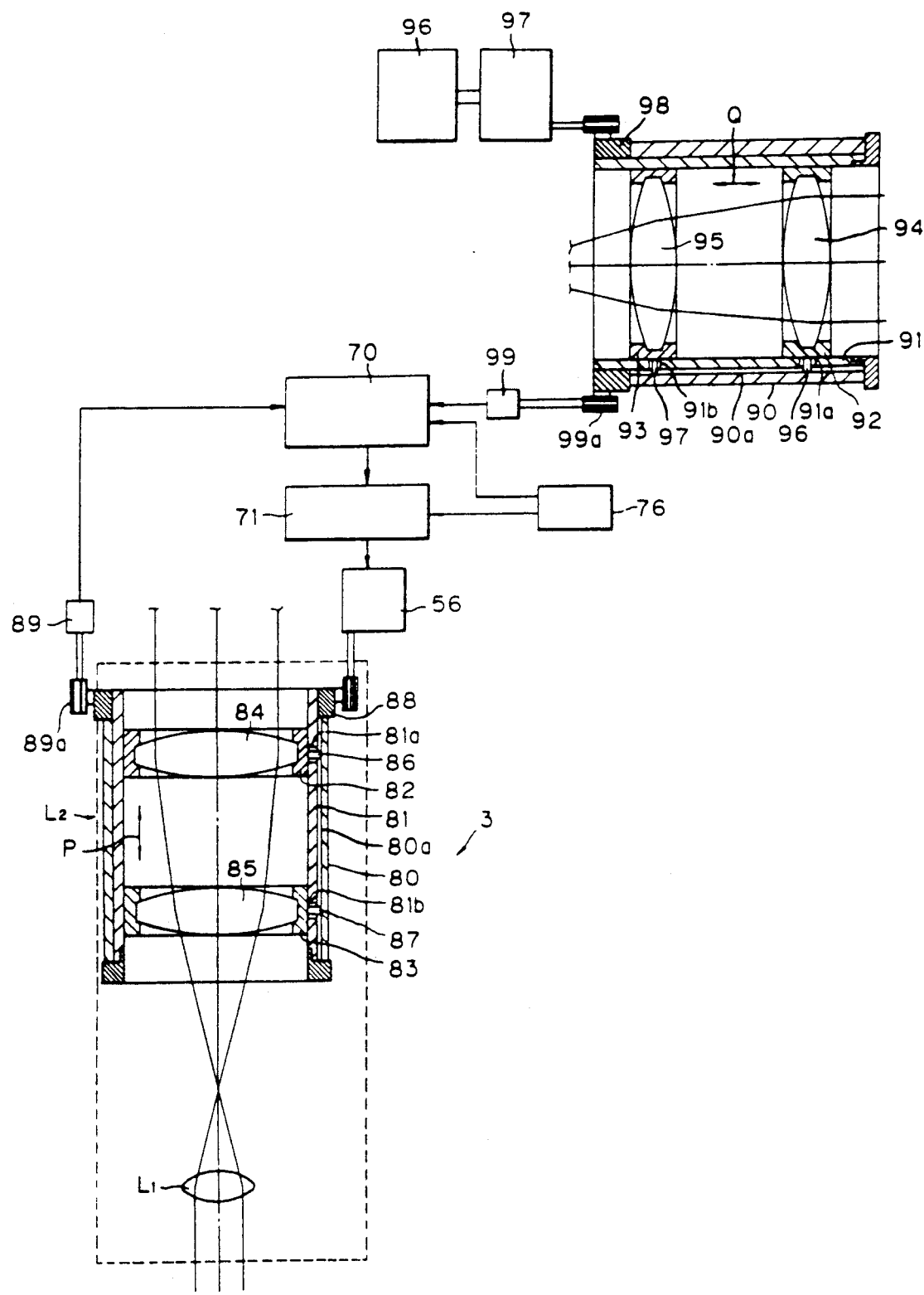
FIG. 27 is a side view of another embodiment of the present invention.

In addition to the example of FIG. 21, the means for determining the beam diameter by the switch 76 can be constructed in such a manner as shown in FIG. 27.

When the subject is very young, for example, and tends to move the eyes during the observation, the above-described embodiment allows the operator to enlarge the spot diameter to obtain a clear image of the eye fundus in spite of slight movement of the subject's eye. Further, the spot diameter can be reduced to obtain a higher resolution.

Figure 6:
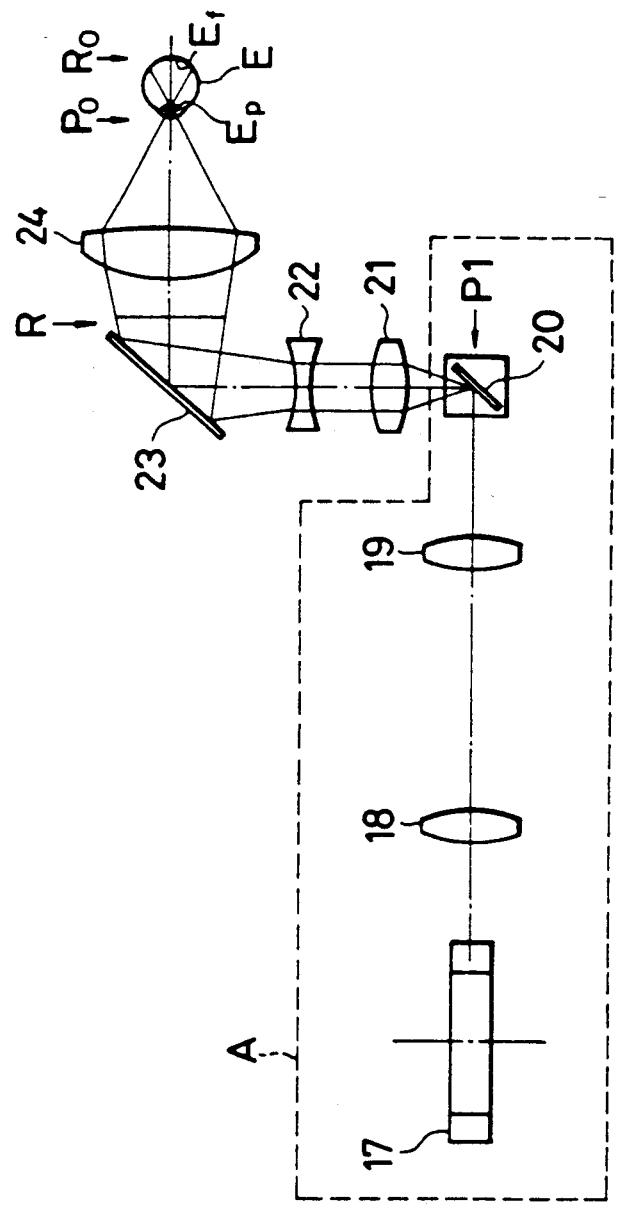
FIG. 6 is a side view showing the arrangement of a portion of the optical system shown in FIG. 5.
Figure 7:
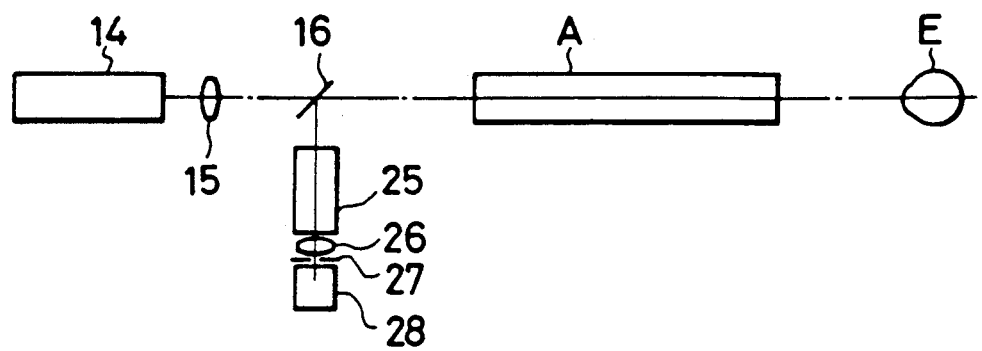
FIG. 7 is a schematic illustration showing the optical system of FIGS. 5 and 6.

FIGS. 5-7 show another embodiment of the present invention.

The optical system in the eye fundus camera shown in FIGS. 5-7 comprises an illuminating optical system for scanning the eye fundus $E_f$ with an illuminating laser light beam, and a light receiving optical system for directing the reflected light from the eye fundus $E_f$ to a light receiving unit.

The illuminating optical system in this embodiment includes a light source in the form of a laser 14, a lens 15, a beam splitter 16, a horizontal scanning member in the form of a polygonal mirror 17, variable lower lenses 18 and 19, a vertical scanning number in the form of a galvanomirror 20, a relay lens 21, a focusing lens 22, a reflecting mirror 23 and an objective lens 24. These elements are arranged in the order in which they are mentioned. The elements from the polygonal mirror 17 to the galvanomirror 20 form in combination an optical scanning device A. In the figures, P indicates a position which is conjugate with the pupil $E_p$ ($P_o$) of the subject's eye E, while R indicates a position which is conjugate with the fundus $E_f$(Ro) of the subject's eye E.

The laser beam from the laser 14 of the illuminating optical system passes through the lens 15 and through the beam splitter 16, and then impinges upon the polygonal mirror. The polygonal mirror 17, while rotating at a high speed, deflects the incident laser beam for scanning in a horizontal plane. The so deflected laser beam is guided through the variable power lenses 18 and 19, the galvanomirror 20, the relay lens 21, the focusing lens 22 and the reflecting mirror 23, and is then projected onto the fundus $E_f$ of the subject's eye E. Then, the galvanomirror 20 is rotated through a predetermined angle each time a horizontal scanning by the polygonal mirror 17 is completed, whereby the horizontal line scanned with the laser light is vertically shifted. Such scanning will form a scanned surface in the fundus $E_f$ of the subject's eye E.

The light receiving optical system comprises the above-mentioned optical system from the beam splitter 16 to the objective lens 24, beam diameter adjusting means in the form of a beam expander 25, a condenser lens 26, a pinhole plate 27 and a light receiving unit in the form of a photodiode 28. The reflected light beam from the eye fundus $E_f$ is guided through the objective lens 24, the reflecting mirror 23, the focusing lens 22, the relay lens 21, the galvanomirror 20, the variable power lenses 14 and 18 and the polygonal mirror 17 and then impinges upon the beam splitter 16 which in turn reflects the incident light beam toward the beam expander 25. The reflected light beam passes through the beam expander 25, whereby the beam diameter is adjusted, and it is then converged at a pin-hole 27a in the pin-hole plate 27 by means of the condenser lens 26 and then enters the photodiode 28.

When there is no shading or eclipse in the scanning device A or the lenses, the diameter of the aperture of the light receiving optical system for receiving the reflected light beam is defined by the effective aperture of the beam expander 25. It is therefore possible to vary the aperture diameter by selectively placing in the optical path one of a set of beam expanders 25 having different magnifications.

Assuming that the magnification at which the pinhole 27a in the pin-hole plate 27, which is situated immediately before the photodiode 28, is geometrically projected onto the eye fundus $E_f$ by the light receiving optical system is "magnification of projection," the resolution will be changed as follows by adjusting the beam expander 25: by increasing the aperture diameter of the light receiving optical system by means of the beam expander 25, the magnification of projection is reduced with the result that the resolution is increased but the depth of field is reduced; conversely, by decreasing the aperture diameter by means of the beam expander 25, the magnification of projection is increased with the result that the resolution is decreased but the depth of field is increased.

Such nature allows the operator to adjust the aperture diameter in view of the subject or of the selected magnification of observation so as to observe the subject's eye E in the most convenient manner. Since the change in the aperture diameter will produce a change in the quantity of the received light, it is desirable to provide, in the optical system, means for automatically adjusting the intensity of illumination in an interconnected manner.

FIG. 7 schematically shows the optical system shown in FIGS. 5 and 6. The optical scanning device A includes the optical elements from the polygonal mirror 17 to the galvanomirror 20, as stated above. In FIG. 7, the optical elements from the above-mentioned relay lens 21 to the objective lens 24 are not shown.

Figure 8:
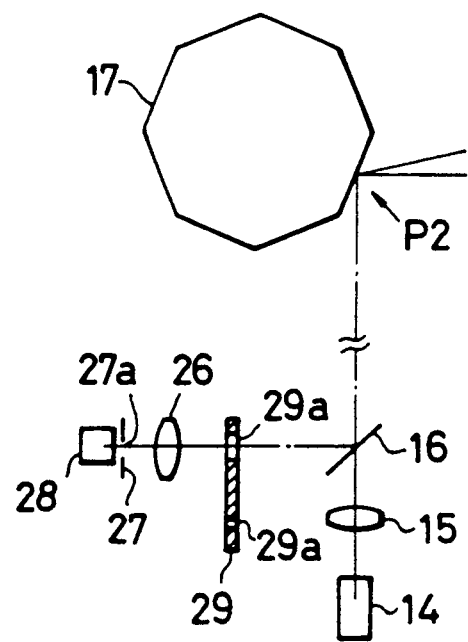
FIG. 8 is an illustration showing an alternative example of the light beam diameter adjusting means shown in FIG. 5.

The embodiments described above include a beam expander 25 as the beam diameter adjusting means. The invention is however not limited to such an arrangement. For example, FIG. 8 shows an alternative beam diameter adjusting means which comprises an aperture plate 29 placed between the beam splitter 16 and the condenser lens 26. The plate 29 is provided with a plurality of circumferentially disposed apertures 29a which have different diameters.

FIGS. 9 through 12 show various arrangements of the beam expander 25 as the beam diameter adjusting means in an eye fundus camera having a single optical scanning device A provided in the common optical path of the illuminating optical system and of the light receiving optical system. In these figures, the optical elements from the relay lens 21 to the objective lens are again not shown.

Figure 9:
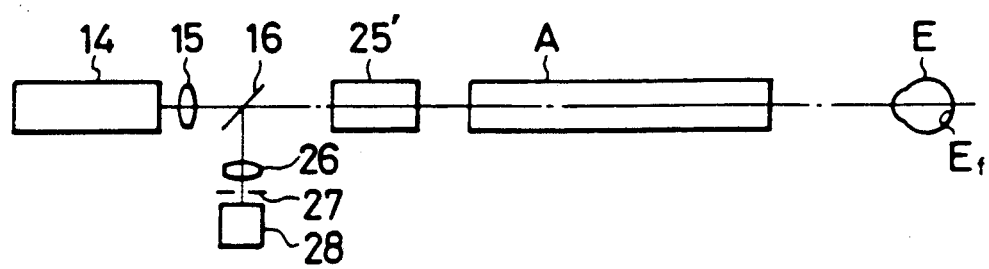
FIGS. 9-15 are schematic illustrations showing further embodiments of the optical system in the laser scanning eye fundus camera according to the present invention.

FIG. 9 shows an embodiment which lacks the beam expander 25 shown in FIG. 5 between the beam splitter 16 and the condenser lens 26, while having the beam expander 25' placed between the beam splitter 16 and the optical scanning device A. In this embodiment, only beam expander 25 allows the operator to simultaneously adjust both the diameter of the laser light spot projected onto the eye fundus $E_f$ from the laser 14, and the diameter of the reflected light beam from the eye fundus $E_f$.

Figure 10:
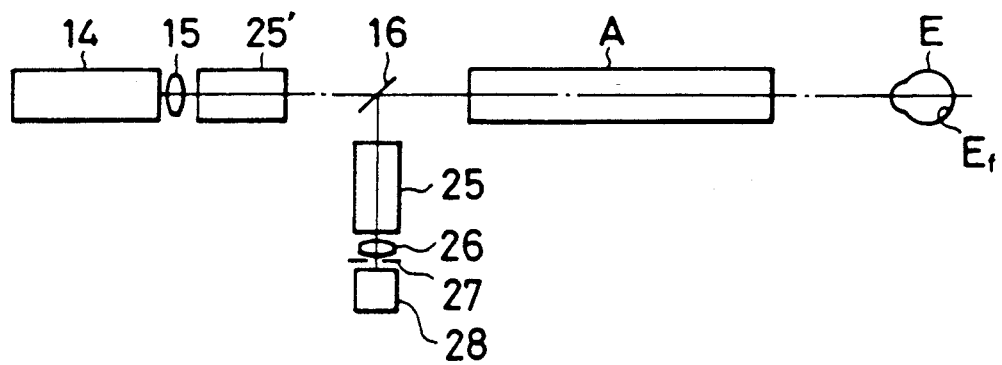

FIG. 10 shows another embodiment having first beam diameter adjusting means in the form of a first beam expander 25' provided between the beam splitter 16 and the system of the lens 15 and the laser 14, and second beam diameter adjusting means in the form of a second beam expander 25 provided between the beam splitter 16 and the condenser lens 26. The present embodiment allows the operator to separately adjust the diameter of the laser light spot projected onto the fundus $E_f$ from the laser 14 and the diameter of reflected light beam from the eye fundus $E_f$.

Figure 11:
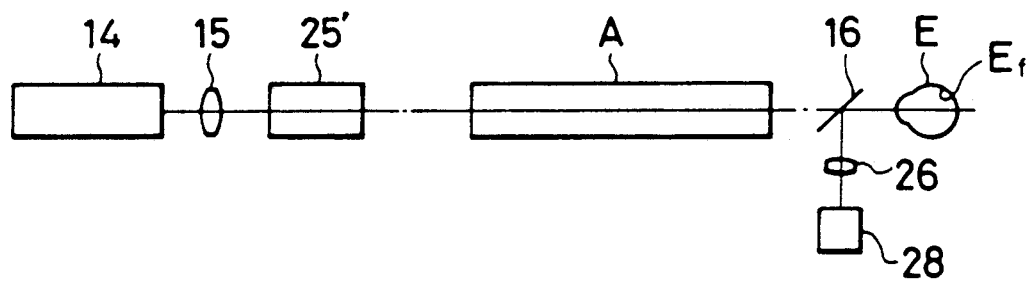

FIG. 11 shows another embodiment which is similar to the embodiment shown in FIG. 9, but in which the beam splitter 16 of the optical system comprising the beam splitter 16, the condenser lens 26 and the photodiode 28 is positioned between the optical scanning device A and the subject's eye E. Here, the reflecting mirror 23 shown in FIG. 5 can be replaced by the beam splitter 16.

Figure 12:
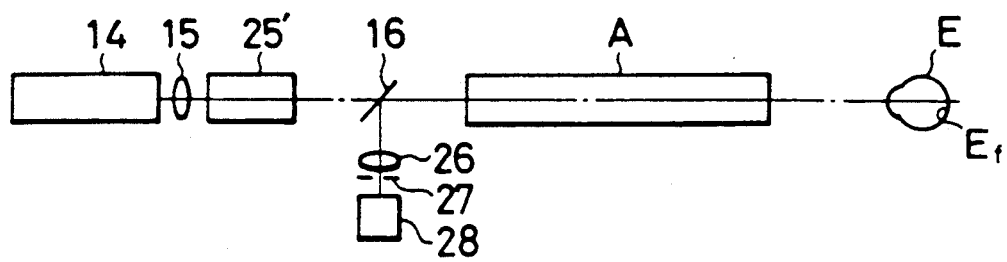

FIG. 12 shows a further embodiment which is similar to that shown in FIG. 10 but which lacks the beam expander 25 between the beam splitter 16 and the condenser lens 26.

Figure 13:
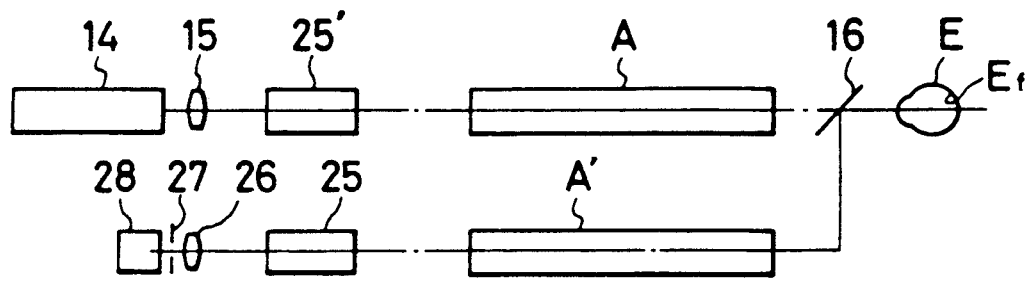
Figure 14:
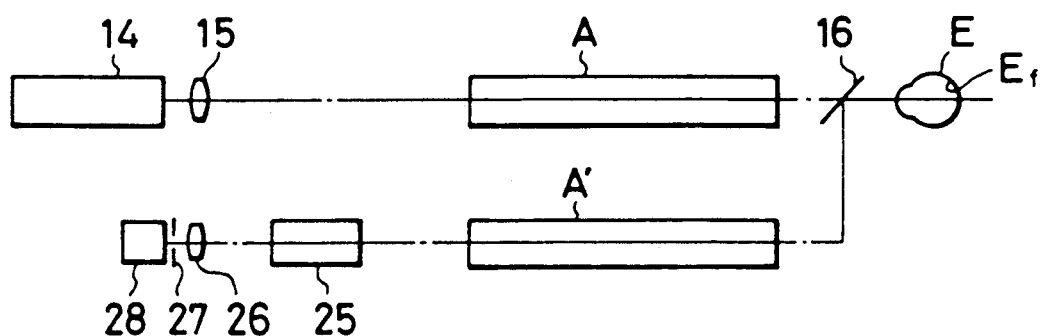
Figure 15:
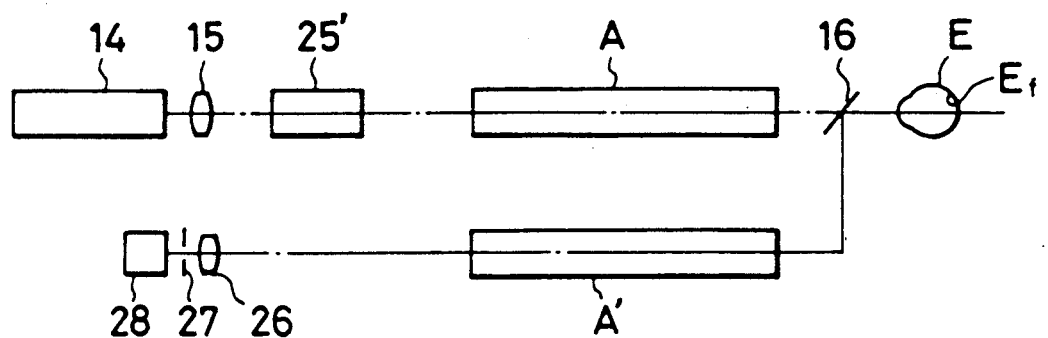
Figure 16:
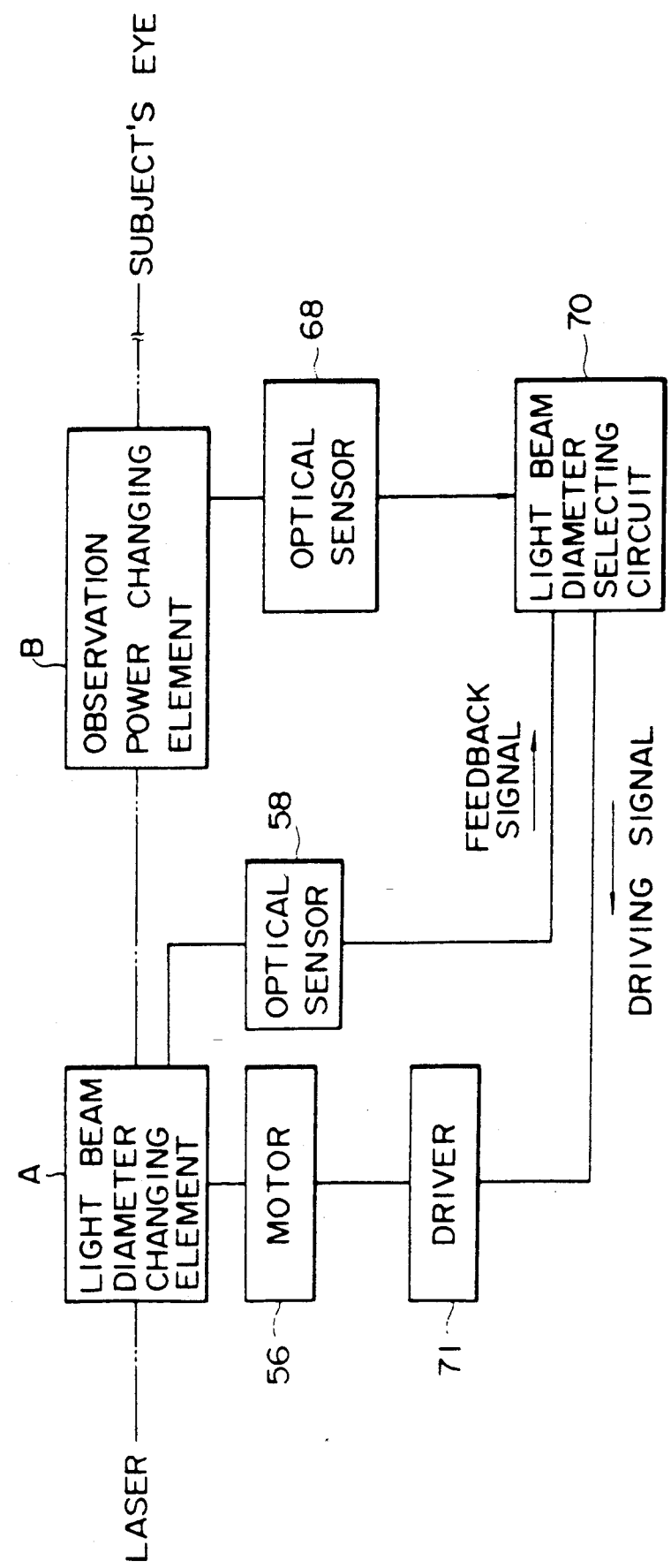
FIG. 16 is a block diagram of an embodiment of the present invention.

FIGS. 13-15 show various arrangements of the beam expander 25 in an eye fundus camera which has the beam splitter 16 placed between the relay lens 21 (also shown in FIGS. 5 and 6) and the subject's eye E, a first optical scanning device A provided between the beam splitter 16 and the system of the lens 15 and the laser 14, and a second optical scanning device A' provided between the beam splitter 16 and the condenser lens 26. The optical elements from the above-mentioned relay lens 21 to the objective lens 24 of these embodiments are not shown in FIGS. 13-15.

The embodiment shown in FIG. 13 includes a first beam diameter adjusting means in the form of a first beam expander 25' provided between the optical scanning device A and the system of the lens 15 and the laser 14, and a second beam diameter adjusting means in the form of a second beam expander 25 provided between another optical scanning device A' and the condenser lens 26.

The embodiment shown in FIG. 14 is similar to that of FIG. 13 but lacks the first beam expander 25'.

The embodiment shown in FIG. 15 is similar to that of FIG. 13 but lacks the second beam expander 25.

As described above, the optical system in a laser scanning eye fundus camera according to the invention comprises: an illuminating optical system for scanning the eye fundus with a laser beam from a light source using an optical scanning device; and a light receiving optical system for directing the reflected light from the eye fundus through the optical scanning device to a light receiving unit. The optical system according to the invention further includes beam diameter adjusting means for adjusting the diameter of said laser light beam. Such arrangement according to the present invention allows to adjust the depth of field by adjusting the aperture diameter of the optical system by means of the beam diameter adjusting means so that test or inspection of even or uniform quality can be ensured for all subjects in spite of variations in their age, experience of medical or ophthalmological tests or inspections, or structure of the eye fundus.

Further, when beam diameter adjusting means for adjusting the diameter of the reflected laser light beam from the eye fundus is provided at least in said light receiving optical system, the aperture diameter of the light receiving optical system can be adjusted in view of the subject's age, experience of test or inspection, or the structure of the eye fundus, so that the depth of field can be easily adjusted to suitably adjust the resolution or to bring into focus the overall eye fundus, especially when the fundus is rugged.

What is claimed is:

1. A laser scanning eye fundus camera, comprising:
   an illuminating optical means for illuminating an eye fundus through an eye pupil by scanning the eye fundus with an illuminating laser light from a laser light source, said illuminating optical means including an optical scanning device;
   a light receiving optical means for directing light reflected from the eye fundus to a light receiving unit, said light receiving optical system including a display device for displaying an image of the eye fundus in response to a signal from said light receiving unit;
   a magnification adjusting means for changing the magnification of the image of the eye fundus on said display device;
   beam diameter adjusting means disposed in said illuminating optical system at a position conjugate with the intended position of the pupil for adjusting the beam diameter of the laser beam projected onto said eye fundus; and
   means for interlocking said beam diameter adjusting means with said magnification adjusting means wherein an adjustment of said magnification adjusting means to increase the magnification causes said beam diameter adjusting means to be adjusted to reduce the beam diameter.

2. The laser scanning eye fundus camera of claim 1, wherein said interlocking means includes means for selecting a light beam diameter.

3. The laser scanning eye fundus camera of claim 2, wherein said interlocking means further includes a first sensor for outputting a first signal to said light beam diameter selecting means corresponding to the adjustment of said beam diameter adjusting means, and a second sensor for outputting a second signal to said light beam diameter selecting means corresponding to the adjustment of said magnification adjusting means.

4. The laser scanning eye fundus camera of claim 3, wherein said first sensor includes a rotary encoder and said second sensor includes a rotary encoder.

5. The laser scanning eye fundus camera of claim 3, wherein said interlocking means further includes switch means, connected to said light beam diameter selecting means, for adjusting the depth of focus of the laser scanning eye fundus camera.

6. The laser scanning eye fundus camera of claim 1, wherein said beam diameter adjusting means includes a rotatable disk with a plurality of beam expanders mounted thereon.

7. The laser scanning eye fundus camera of claim 6, wherein said beam diameter adjusting means further includes a motor connected to a shaft via a gear means, the shaft being connected to the rotatable disk.

8. The laser scanning eye fundus camera of claim 1, wherein said magnification adjusting means includes a rotatable disk with a plurality of beam expanders mounted thereon.

9. The laser scanning eye fundus camera of claim 8, wherein said magnification adjusting means further includes a motor connected to a shaft via a gear means, the shaft being connected to the rotatable disk.

10. The laser scanning eye fundus camera of claim 1, wherein said beam diameter adjusting means includes a first lens and second lens combination being aligned on an optical axis, and means for moving the first and second lenses relative to one another along the optical axis.

11. The laser scanning eye fundus camera of claim 10, wherein said moving means includes a motor connected to a cam drum via a gear means, said cam drum being rotated by said motor through said gear means, said cam drum connected to a first lens frame, containing said first lens, via a pin and key groove assembly and a second lens frame, containing said second lens, via a pin and key groove assembly such that the rotation of said cam drum causes said first lens and said second lens to move relative to one another along the optical axis.

12. The laser scanning eye fundus camera of claim 1, wherein said magnification adjusting means includes a first lens and second lens combination being aligned on an optical axis, and means for moving the first and second lenses relative to one another along the optical axis.

13. The laser scanning eye fundus camera of claim 12, wherein said moving means includes a motor connected to a cam drum via a gear means, said cam drum being rotated by said motor through said gear means, said cam drum connected to a first lens frame, containing said first lens, via a pin and key groove assembly and a second lens frame, containing said second lens, via a pin and key groove assembly such that the rotation of said cam drum causes said first lens and said second lens to move relative to one another along the optical axis.

14. The laser scanning eye fundus camera of claim 1, wherein said interlocking means includes a means for mechanically linking said beam diameter adjusting means and said magnification adjusting means.

15. The laser scanning eye fundus camera of claim 14, wherein said means for mechanically linking includes a motor connected to a first shaft via a first gear means and connected to a second shaft via a second gear means, said first shaft being connected to a first rotatable disk and said second shaft being connected to a second rotatable disk.

16. The laser scanning eye fundus camera of claim 15, wherein said first and second rotatable disks each include a plurality of beam expanders mounted thereon.

17. The laser scanning eye fundus camera of claim 1, in which said illumination optical means has a horizontal scanning member and a laser, and in which said beam diameter adjusting means is disposed between the horizontal scanning member and the laser.

18. The laser scanning eye fundus camera of claim 1, in which said light receiving optical means and said illuminating optical means have a common optical scanning device, in which said beam diameter adjusting means is disposed between the laser light source and the optical scanning device, and in which the reflected light from the eye fundus is directed to the light receiving unit through a beam splitter disposed between said laser light source and the optical scanning device.

19. The laser scanning eye fundus camera of claim 1, in which said light receiving optical means and said illuminating optical means have a common optical scanning device, in which said beam diameter adjusting means is disposed between the laser light source and the optical scanning device, and in which the reflected light from the eye fundus is directed to the light receiving unit through a beam splitter disposed between said beam diameter adjusting means and said optical scanning device.

20. The laser scanning eye fundus camera of claim 1, in which said beam diameter adjusting means is disposed between the laser light source and the optical scanning device, and in which the reflected light from the eye fundus is directed to said light receiving unit through a beam splitter placed between the subject's eye and the optical scanning device.

21. The laser scanning eye fundus camera of claim 1, in which said light receiving optical means and said illuminating optical means have a common optical scanning device, in which said beam diameter adjusting means is disposed between the laser light source and the optical scanning device, in which the reflected light from the eye fundus is directed to the light receiving unit through a beam splitter disposed between said beam diameter adjusting means and said optical scanning device, and in which second beam diameter adjusting means, separate from said beam diameter adjusting means, is disposed between the beam splitter and the light receiving unit.

22. The laser scanning eye fundus camera of claim 1, in which said light receiving optical means and said illuminating optical means have a common optical scanning device, in which the reflected light from the eye fundus is directed to the light receiving unit through a beam splitter disposed between the optical scanning device and the laser light source, and in which beam diameter adjusting means is disposed between said beam splitter and the light receiving unit.

23. The laser scanning eye fundus camera of claim 1, in which said illuminating optical means includes a first optical scanning device for scanning the illuminating laser light, said light receiving optical means includes a second optical scanning device for scanning the reflected light, and said beam diameter adjusting means is disposed between the laser light source and said first optical scanning device.

24. The laser scanning eye fundus camera of claim 1, in which said illuminating optical means includes a first optical scanning device for scanning the illuminating light, said light receiving optical means includes a second optical scanning device for scanning the reflected light, and said beam diameter adjusting means is disposed between the light receiving unit and the second optical scanning device.

25. The laser scanning eye fundus camera of claim 1, in which said illuminating optical means includes a first optical scanning device for scanning the illuminating light, and said light receiving optical means includes second optical scanning device for scanning the reflected light, wherein a first beam diameter adjusting means is disposed between the laser light source and the first optical scanning device, and wherein a second beam diameter adjusting means is disposed between the light receiving unit and the second optical scanning device.

26. A laser scanning eye fundus camera, comprising:
an illuminating optical means for illuminating an eye fundus through an eye pupil by scanning the eye fundus with an illuminating laser light from a laser light source, said illuminating optical means including an optical scanning device;
a light receiving optical means for directing light reflected from the eye fundus to a light receiving unit, said light receiving optical system including a display device for displaying an image of the eye fundus in response to a signal from said light receiving unit;
magnification adjusting means for changing the magnification of the image of the eye fundus on said display device;
beam diameter adjusting means disposed in said illuminating optical system at a position conjugate with the intended position of the pupil, for adjusting the beam diameter of the laser beam projected onto said eye fundus; and
means for interlocking said beam diameter adjusting means with said magnification adjusting means wherein an adjustment of said magnification adjusting means to decrease the magnification causes said beam diameter adjusting means to be adjusted to expand the beam diameter.

* * * * *